US008296077B2

(12) United States Patent
Almiman

(10) Patent No.: US 8,296,077 B2
(45) Date of Patent: Oct. 23, 2012

(54) FOOD ADDITIVE DETECTOR

(75) Inventor: Fozeyah Saleh Almiman, Riyadh (SA)

(73) Assignee: King Saud University, Riyadh (SA)

( * ) Notice: Subject to any disclaimer, the term of this patent is extended or adjusted under 35 U.S.C. 154(b) by 379 days.

(21) Appl. No.: 12/569,991

(22) Filed: Sep. 30, 2009

(65) Prior Publication Data

US 2010/0088038 A1    Apr. 8, 2010

Related U.S. Application Data

(60) Provisional application No. 61/102,768, filed on Oct. 3, 2008.

(51) Int. Cl.
*G01N 33/02* (2006.01)
*G06F 19/00* (2011.01)
(52) U.S. Cl. .................... 702/22; 436/2; 705/2
(58) Field of Classification Search ............ 702/22, 702/23, 32, 99, 101, 104, 116, 122, 123; 422/68.1, 400, 401; 436/2; 600/300; 705/2
See application file for complete search history.

(56) References Cited

U.S. PATENT DOCUMENTS 7,514,262 B2 * 4/2009 Ribi ............................ 436/2
2004/0078219 A1 * 4/2004 Kaylor et al. ................ 705/2

* cited by examiner

*Primary Examiner* — John H Le
(74) *Attorney, Agent, or Firm* — Hart IP Law & Strategies, LLC

(57) ABSTRACT

Systems and methods for a handheld food additive detector are described. In one aspect, the food additive detector includes a test strip treated with or comprising chemical(s) reactive to at least one target characteristic (e.g., additive(s), compound(s) created as a result of stale/old food, etc.). Responsive to a food sample being placed on the strip, a sensor operatively coupled to the handheld device measures one or more of the strip characteristics (e.g., color, contrast, etc.) resulting from placement of the sample on the strip. The device analyzes the sensor measurement value(s) to determine presence, quantity, concentration, percentage, relative amount, and/or so on, of the target food additive(s), or other characteristics of the food that pertain, for example, to freshness or staleness. Results of the analysis are presented to a user.

21 Claims, 3 Drawing Sheets

FOOD ADDITIVE DETECTOR

RELATED APPLICATIONS

This patent application claims priority to U.S. Provisional Patent Application Ser. No. 61/102,768, filed Oct. 3, 2008, titled "Assessing Characteristics of Food", and which is hereby incorporated by reference.

BACKGROUND

Safe ingredients and freshness are generally desired characteristics of food products. Yet, consumers are not always able to determine the components of food and/or freshness of food before purchasing or consuming the food. Often, simply smelling or looking at food may not be sufficient to determine the safety and freshness of the food before consumption. Additionally, food allergies are commonplace, and it may be difficult for a consumer to determine whether any allergy-causing ingredients are present in a food product. For instance, a food's characteristics may not be readily apparent and/or correctly represented on a package label. Allergic reactions to food may vary from minor discomfort to death. Moreover, although certain food product ingredients may not be harmful in small quantities, those same ingredients may be harmful if present in excessive quantities. For instance, food additives may be present in food products in harmful quantities (e.g., exceeding domestic and/or international safety standards). A consumer may not be able to determine the safety of food from simple sight or smell indicators.

SUMMARY

Systems and methods for a handheld food additive detector are described. In one aspect, the food additive detector includes a test strip that has been treated with chemical(s) reactive to at least one target food characteristic such as an additive. An end-user places a sample of a food product to be tested for the one or more food characteristics on the test strip. Certain characteristics of the test strip ("strip characteristics") will change responsive to contact with the food sample. A sensor operatively coupled to the handheld food additive detector measures one or more of the strip characteristics (e.g., color, contrast, etc.). In one implementation, such sensor measurement operations are automatically performed responsive to the food sample being detected/placed on the test strip, a button press, and/or so on, to generate a set of measurement values. A processing unit operatively coupled to the handheld food analysis detector analyzes the sensor measurement value(s) to determine presence, quantity, concentration, percentage, relative amount, and/or so on, of the target food additive(s), or other characteristics of the food that pertain, for example, to freshness or staleness. Results of the analysis are presented to the end user.

This Summary is provided to introduce a selection of concepts in a simplified form further described below in the detailed description. This Summary is not intended to identify key features or essential features of the claimed subject matter, nor is it intended to be used as an aid in determining the scope of the claimed subject matter. Additional features, advantages, and embodiments of the apparatus and methods for assessing characteristics of food are set forth or apparent from consideration of the following detailed description, drawings, and claims. Moreover, it is to be understood that both the foregoing Summary and the following detailed description are exemplary and intended to provide further explanation without limiting the scope of the apparatus and methods for assessing characteristics of food, as claimed.

DETAILED DESCRIPTION

Overview

Figure 1:
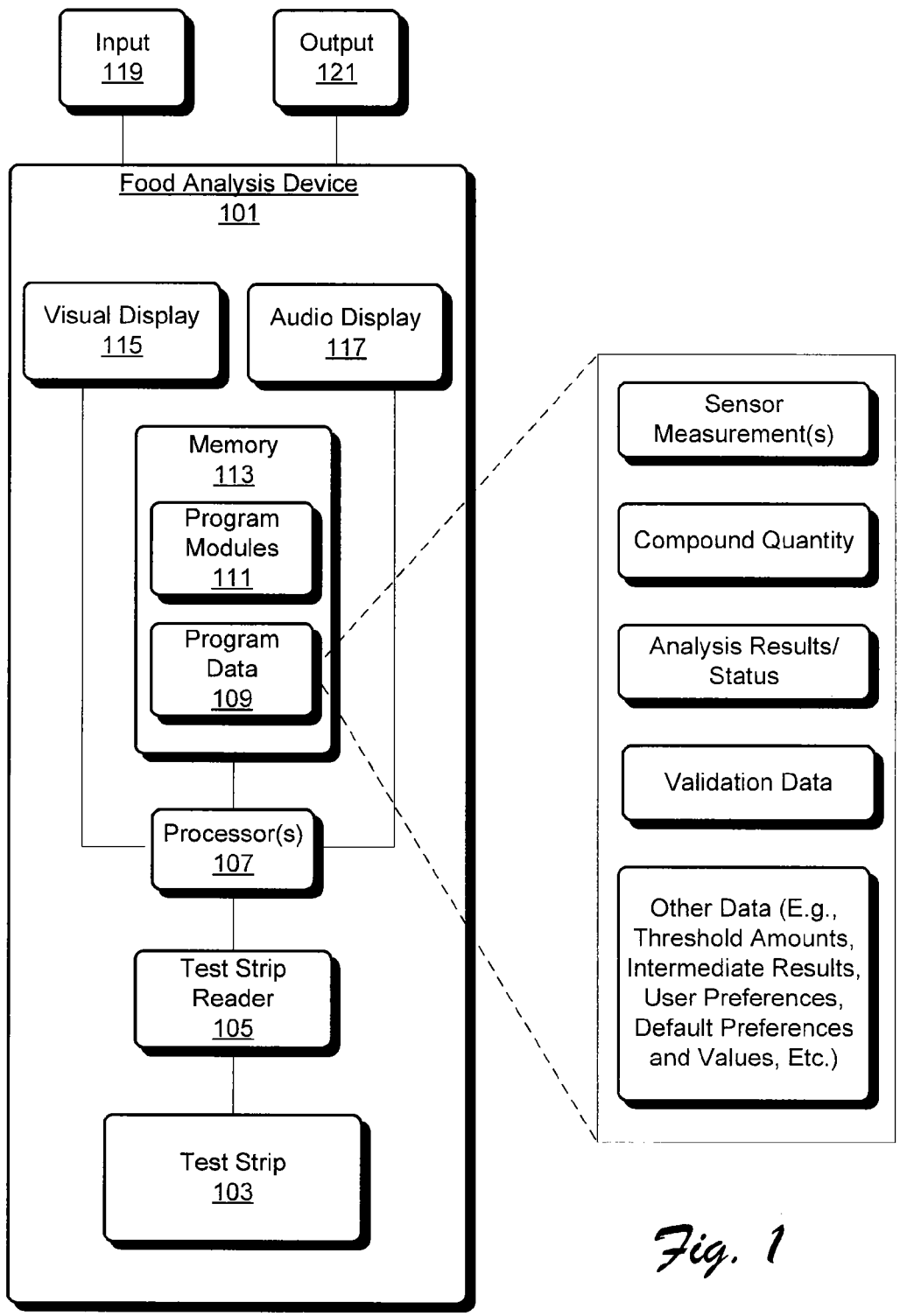
FIG. 1 shows an exemplary apparatus for assessing the status of food, according to one embodiment.

Traditionally, a person determines components of a food product (food) by taking the food to an institutional laboratory, wherein sophisticated and generally expensive technology may be utilized to examine the food and determine its constituent makeup (components). In such a scenario, it is possible that the person will have to wait for hours, days, or weeks to receive results of the component analysis for evaluation. Moreover, unless the user has straightforward and prioritized access to such a laboratory, obtaining food component analysis results will generally be time consuming and expensive. Clearly, this is not a viable solution in many situations. The systems and methods described below with respect to FIGS. 1-3 address these and other limitations of conventional techniques to determine components and characteristics of food products, and present such component results and/or characteristics to an end user for evaluation.

In one implementation, for example, a handheld portable apparatus for food analysis is described that provides substantially immediate food component analysis results to a user (e.g., via a display device, a printout, audio output, and/or so on). In this implementation, the user provides a sample of food (e.g., in contact with or in proximity to) to an analyzing structure in the portable device for chemical analysis of the food. Such analysis, for example, may indicate the presence, absence, amounts (e.g., parts-per-million, milligrams, grams, ounces, percentages, and/or so on) of components of a given food product (e.g., on a per sample basis, etc.). Such components may include, for example, one or more of ingredients, allergens, preservatives, colorings/dyes, flavorings, etc. The components and respective component amounts identified via such food analysis are arbitrary, being a function of the characteristics of the food being analyzed, the particular analysis algorithms implemented by the apparatus for food analysis, and configurable functional characteristics of the apparatus. In one implementation, the apparatus stores food analysis results in a computer-readable memory (local and/or remote memory) for later use (e.g., in association with subsequent and/or prior food analysis calculations and/or selective recall by a user).

In one implementation, for example, the food analysis methods and apparatus provide a user interface (e.g., keys, voice recognition, and/or other selection mechanisms) to allow a user to specify a particular set of characteristics (e.g., components, a relative indication of freshness, and/or so on) of the food for which the apparatus is to analyze the food and present corresponding results to the user. In another implementation, the analyzing structure is a test strip (e.g., a consumable, plastic, reusable, permanent, and/or disposable element) containing chemicals that react with particular ones of food product components. In another implementation, such characteristics or analysis parameters are automatically selected or predefined for the apparatus. In one implementation, the test strip is porous and manufactured in a rectangular shape, the test strip may include an internal cavity to hold respective reactive materials/chemicals.

For example, if a user desires to identify an emulsion material such as starch in a food sample, the test strip may be treated with, or otherwise comprise, iodine. In this example, after contact with a food sample comprising starch, the treated test strip will change color (blue) as a function of the level of starch in the sample. A visual sensor in the food analysis system measures, for example, contrast of the resulting color on the strip to determine an amount or level of starch in the sample. Processing means in the food analysis system converts the contrast measurement into a result for presentation to the user. For instance, the user may wish to determine mere presence of the additive. In another example, the user may desire to determine a relative amount of starch and the food sample, such as a percentage, a concentration, or a high, low, or medium amount of starch in the food sample as compared to a baseline/threshold amount.

In another example, a test strip for the food analysis device of this disclosure is designed to identify characteristics of a food sample that comprises Benzo-A-Pyren ($C_{20}H_{12}$). Upon contact with the test strip, a food sample comprising this chemical will cause the strip to change color based on the concentration of the chemical in the sample. A photo sensor in the food analysis apparatus measures the color characteristics to determine a concentration of the chemical in the sample. Corresponding results are then presented in one or more forms or modes to the user.

FIG. 1 shows an exemplary food analysis device/apparatus 101 for assessing characteristics of food according to one embodiment. In one implementation, a small sample of a food is supplied to the apparatus 101. The sample may be a liquid, solid, or a combination of liquid and solid. In this example, the sample is placed in contact with a test strip 103 operatively coupled to the apparatus 101. The food sample may be solid, or otherwise. Also, the test strip 103 may be subjected to a liquid portion (e.g., dipped into) of the sample food product for analysis. A test strip reader 105 utilizes one or more chemical analysis techniques to determine the presence, absence, or amount of a selected and/or predetermined sets of compounds in the sample based upon a reading from the test strip 103. Results of the test strip reader analysis (shown as a respective portion of "Program Data" 109) are output to processor 107.

Processor 107 executes computer program instructions in one or more computer program modules 111 to process the results to determine status (e.g., composition and/or relative freshness) of the food product. The status of the food product may be stored in the program data 109 portion of memory 113 that is operatively coupled to the processor 107. The status, shown as output 121, of the food product may be output to a visual display 115 and/or an auditory display 117. The audio output may include the name of a detected compound (or set of compounds), an indication of whether the food is fresh, an indication of whether the food product is safe to eat (e.g., in view of a user-input set of criteria such as known food allergies, user preferences, medications currently being taken, etc.), and/or so on. The output 121 may include, for example, the name of the selected compound, the type, quantity, and/or concentration in the food product. The output may also include comparisons to applicable standards. The applicable standards may be predetermined and may be set, for example, by county, state, or federal regulations. The apparatus 101 may be preset to meet regulations in a particular location, a particular cultural setting, desired diet, etc. The output may be stored in the memory 111 for future reference and/or reporting (e.g., to applicable regulatory agencies, etc.).

A visual display 115 may be an LED or other type of screen. The auditory display 117 may be an audio device, such as a speaker. In one implementation, apparatus 101 has data handling capabilities, wherein data is input to the system with an input device 119, such as a keypad, keyboard, voice recognition, USB, etc. Additionally, data from the memory 111 may be downloaded by an output device 121, such as a cable, wireless, or infrared connection to an external computing device to store, display, or further analyze the test results. Although displays 115 and 117 are shown as being incorporated in the device 101, other embodiments of the device 101 do not incorporate one or more of the displays 115 and 117, but rather, one or more of the displays are operatively coupled to the device to receive output 121 for presentation to the user. Additionally, although the device is shown with both displays 115 and 117, other embodiments of the device comprise, or are remotely coupled, to less or more of such displays.

Figure 2:
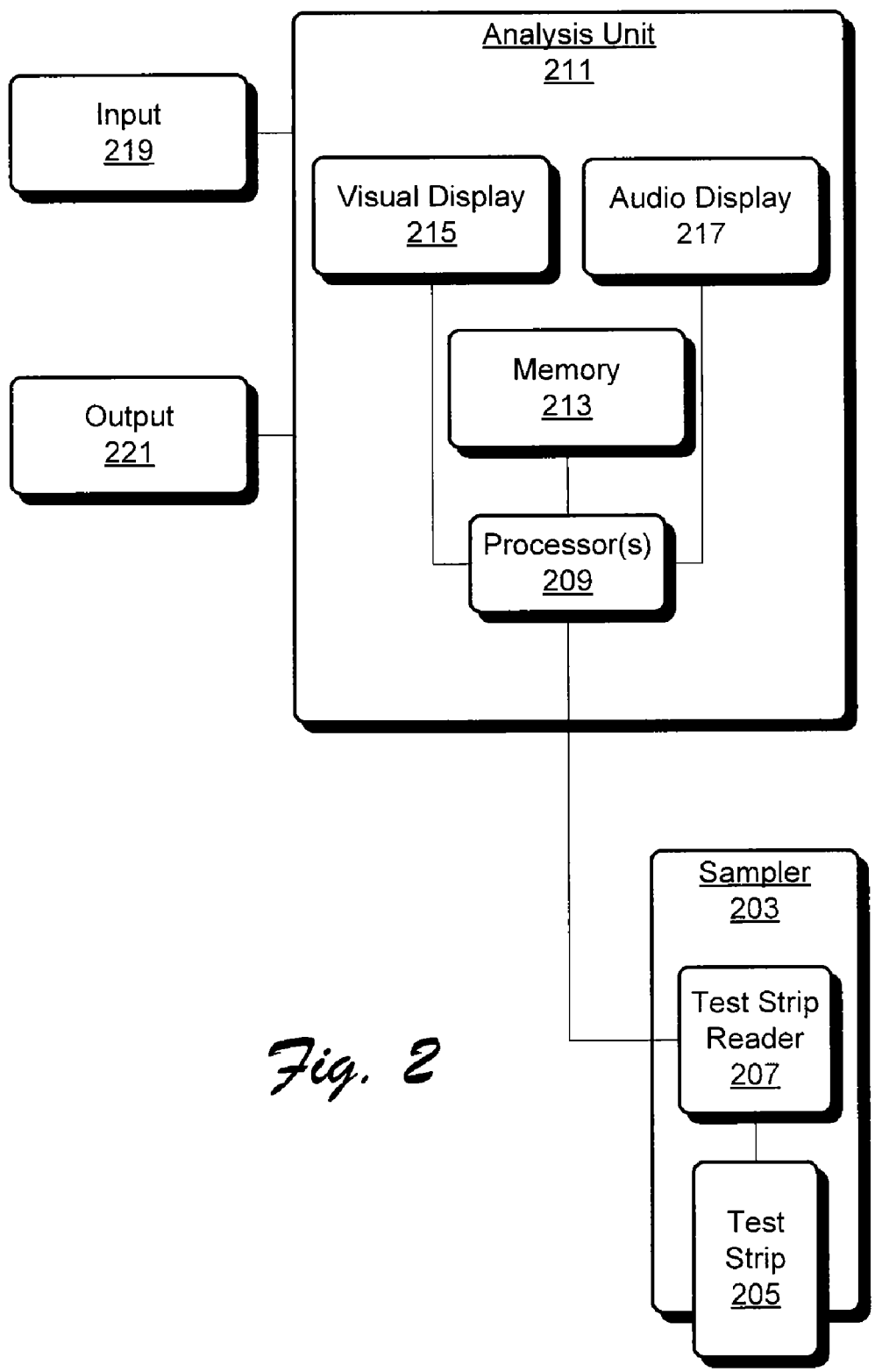
FIG. 2 shows an exemplary apparatus for assessing the status of food, according to one embodiment.

FIG. 2 shows an exemplary apparatus 201 for assessing characteristics of food according to one embodiment. The apparatus of FIG. 2 generally operates similarly to the exemplary apparatus 101 of FIG. 1. In FIG. 2, a cylindrical or other shaped sampler 203 may be used to take a sample of a food product. A test strip 205 may be held within the sampler 203. As the food sample is drawn into the sampler 203, a test strip reader 207 may determine food characteristics such as the presence, absence, or amount of a selected compound in the sample based upon a reading from the test strip 205. The results of the test strip reader analysis may be output to a processor 209, which may be located on a separate analysis unit 211. The processor 209 executed computer program instructions in one or more computer program modules located in memory 213 to process the results and determine status of the food product. The status of the food product (a respective portion of program data in memory 213) may be output, to a visual display 215, an auditory display 217, or other type of output device such as a bar code writer or printer (e.g., to accordingly label the food or a food container). A visual display 215 may be an LED or other type of screen. The auditory display 217 may be an audio device, such as a speaker. The audio output may include the name of the compound and whether the food product is safe to eat in view of a predetermined and possibly configurable set of criteria. Such criteria may be provided as user input 219.

Furthermore, a detector of FIGS. 1 and/or 2 may detect/determine/calculate a validation date and/or chemicals caused by spoiling food products to determine whether the food product is fresh or spoiled. Products may be marked with validation data, such as use-by or sell-by dates. This information may be embedded in scanner-readable devices, such as bar codes and/or radio frequency identification tags. The apparatus may include a reader for accessing the validation data to determine suitability of the food product for consumption. In another exemplary implementation, the detector may determine the presence of chemicals associated with spoiling food products. The chemicals may be detected in a similar process as used to determine the presence, absence, or amount of a selected compound in the food product. Threshold levels of these chemicals may be stored in a memory. The user is notified as to whether the food product is safe to eat by an output device.

Apparatus 201 may have data handling capabilities. Data may be input to the system with an input device 219, such as a keypad, keyboard, USB, etc. Data from the memory 213 may be communicated to an output device 221, e.g., via a cable, wireless, or infrared connection, such as a bar code writing device, a remote computing device to store, display, or further analyze the test results, and/or so on.

Figure 3:
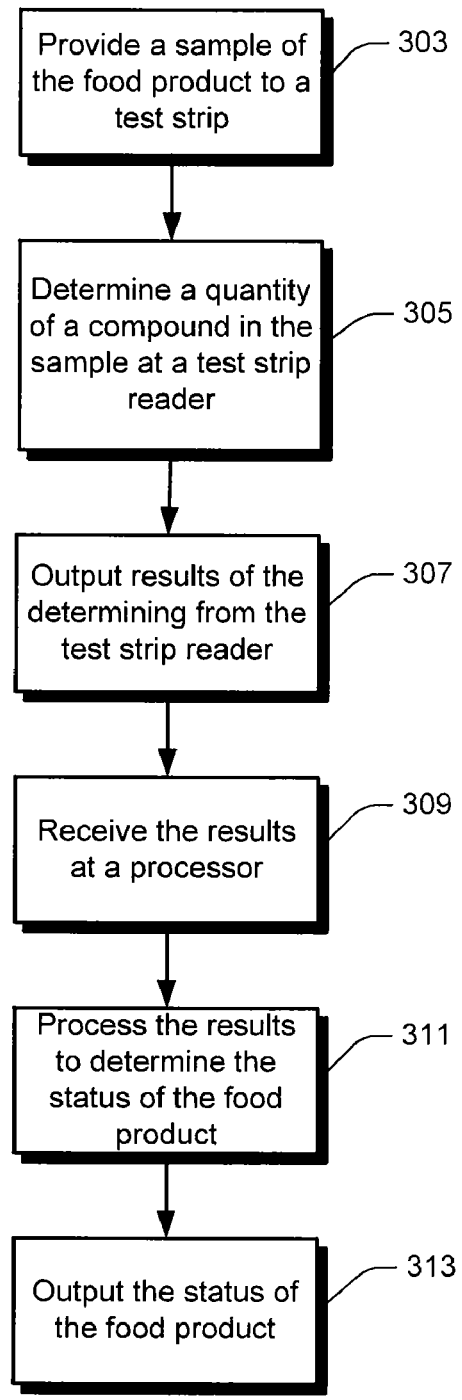
FIG. 3 shows an exemplary method for assessing the status of food, according to one embodiment.

FIG. 3 shows an exemplary procedure 301 for assessing characteristics of food according to one embodiment. A sample of the food product may be provided to a test strip 303. A quantity of a compound in the sample may be determined at a test strip reader 305. The results of the determining from the test strip reader may be output 307. The results may be received at a processor 309. The processor may process the results to determine the status of the food product 311. The status of the food product may be output to a user 313 for evaluation.

The above-described exemplary embodiments of apparatus and methods for assessing characteristics of food via a food additive detector device/apparatus are presented for illustrative purposes only. While these apparatus and methods for assessing characteristics of food are satisfied by embodiments in many different forms, it is understood that the present disclosure is to be considered as exemplary and is not intended to limit the described systems and methods to the specific embodiments illustrated and described herein. Numerous variations may be made by persons skilled in the art without departure from the spirit of this description. Moreover, features described in connection with one embodiment may be used in conjunction with other embodiments, even if not explicitly stated above. The scope of the apparatus and methods for assessing characteristics of food will be measured by the appended claims and their equivalents. The abstract and the title are not to be construed as limiting the scope of the claims, as their purpose is to enable the appropriate authorities, as well as the general public, to quickly determine the general nature of the described systems and methods. In the claims that follow, unless the term "means" is used, none of the features or elements recited therein should be construed as means-plus-function limitations pursuant to 35 U.S.C. §112, ¶6.

The invention claimed is:

1. An apparatus for assessing status of a food product, the apparatus comprising:
   a test strip for receiving a sample of the food product;
   a test strip reader coupled to the test strip for determining a quantity of a compound in the sample and outputting results of the determination;
   a processor configured to receive the results from the test strip reader and configured to determine a freshness status of the food product; and
   a display for presenting the freshness status of the food product to a user.

2. The apparatus of claim 1 wherein the test strip reader is configured to detect test strip characteristics associated with more than one compound.

3. The apparatus of claim 1, further comprising a memory for storing the results from the test strip reader.

4. The apparatus of claim 1 wherein the status of the food product is determined by comparing the quantity of a compound in the sample with regulations of the quantity of the compound in the food product.

5. The apparatus of claim 1 wherein the display is for visual or audible presentation of the status.

6. The apparatus of claim 1 wherein the display is a printer or a bar code generating device.

7. The apparatus of claim 1, further comprising a housing for the test strip.

8. The apparatus of claim 1, further comprising a scanner for reading scanner-readable media comprising validation data.

9. The apparatus of claim 1 wherein the apparatus is a user portable small form factor device.

10. An apparatus for assessing status of a food product, the apparatus comprising:
    means for receiving a sample of the food product;
    means for determining a quantity of a compound in the sample and outputting results of the determination;
    means for receiving the results from the test strip reader;
    means for determining a freshness status of the food product based on the results of the determination of the quantity of the compound in the sample; and
    means for outputting the freshness status of the food product.

11. The apparatus of claim 10 wherein the means for determining the quantity of the compound in the sample detects one or more compounds.

12. The apparatus of claim 10, further comprising a means for storing the results from the test strip reader.

13. The apparatus of claim 10 wherein the status of the food product is determined by comparing the quantity of a compound in the sample with regulations of the quantity of the compound in the food product.

14. The apparatus of claim 10 wherein the means for outputting the status of the food product is a visual display or an auditory signal.

15. The apparatus of claim 10 wherein the freshness status comprises an indication of the relative freshness of the food product.

16. The apparatus of claim 10, further comprising:
    means for calculating, from the freshness status, a use-by date or sell-by date or validation data; and
    means for presenting the validation data to a user.

17. The apparatus of claim 10, further comprising:
    means for reading scanner-readable devices containing validation data; and
    means for confirming or rejecting the validation data based on the status.

18. A method for calculating a validation date for a food product, the method comprising:
    receiving a sample of the food product to a test strip;
    determining characteristics of a compound in the sample from the test strip;
    analyzing, in view of threshold amounts of the compound, the characteristics to determine a freshness status of the food product;
    calculating, based on the freshness status, a validation date comprising a use-by date or a sell-by date; and
    presenting the validation date to a user.

19. The method of claim 18 wherein presenting the validation date comprises printing the validation date in a media designed to attach to the food product or a container associated with the food product.

20. The method of claim 19 wherein the validation date is a bar code.

21. The method of claim 18, further comprising outputting information associated with the freshness status to a user, the information comprising one or more of a result associated with an amount of the compound a relative freshness indication.

* * * * *